United States Patent [19]

Hubble, III et al.

[11] Patent Number: 4,989,985
[45] Date of Patent: Feb. 5, 1991

[54] DENSITOMETER FOR MEASURING SPECULAR REFLECTIVITY

[75] Inventors: Fred F. Hubble, III; Theresa K. Mattioli, both of Rochester, N.Y.

[73] Assignee: Xerox Corporation, Stamford, Conn.

[21] Appl. No.: 246,242

[22] Filed: Sep. 19, 1988

[51] Int. Cl.$^5$ ............................................. G01N 21/47
[52] U.S. Cl. ........................................ 356/445; 356/446
[58] Field of Search ................................. 356/445, 446

[56] References Cited

U.S. PATENT DOCUMENTS

| | | | |
|---|---|---|---|
| 2,315,282 | 3/1943 | Snow | 356/446 |
| 4,054,391 | 10/1977 | Witte | 356/209 |
| 4,226,541 | 10/1980 | Tisue | 356/446 |
| 4,284,356 | 8/1981 | Heilman | 356/429 |
| 4,553,033 | 11/1985 | Hubble, III et al. | 250/353 |
| 4,652,115 | 3/1987 | Palm et al. | 355/327 |
| 4,796,065 | 1/1989 | Kanbayashi | 355/208 |

Primary Examiner—Richard A. Rosenberger
Attorney, Agent, or Firm—H. Fleischer; J. E. Beck; R. Zibelli

[57] ABSTRACT

An infrared densitometer which measures the reduction in the specular component of reflectivity as marking particles are progressively deposited on a moving photoconductive belt. Collimated light rays are projected onto the marking particles. The light rays reflected from at least the marking particles are collected and directed onto a photodiode array. The photodiode array generates electrical signals proportional to the total flux and the diffuse component of the total flux of the reflected light rays. Circuitry compares the electrical signals and determines the difference therebetween to generate an electrical signal proportional to the specular component of the total flux of the reflected light rays.

6 Claims, 5 Drawing Sheets

DENSITOMETER FOR MEASURING SPECULAR REFLECTIVITY

This invention relates generally to an electrophotographic printing machine, and more particularly concerns an improved infrared densitometer for use therein to detect a reduction in the specular reflectivity as toner particles are progressively deposited on a photoconductive member.

In an electrophotographic printing machine, the photoconductive member is charged to a substantially uniform potential to sensitize the surface thereof. The charged portion of the photoconductive member is exposed to a light image of an original document being reproduced. Exposure of the charged photoconductive member selectively dissipates the charge thereon in the irradiated areas. This records an electrostatic latent image on the photoconductive member corresponding to the informational area contained within the original document being reproduced. After the electrostatic latent image is recorded on the photoconductive member, the latent image is developed by bringing marking or toner particles into contact therewith. This forms a powder image on the photoconductive member which is subsequently transferred to a copy sheet. The copy sheet is heated to permanently affix the marking particles thereto in image configuration.

Various types of development systems have hereinbefore been employed. These systems utilize two component developer mixes or single component developer materials. Typical two component developer mixes employed are well known in the art, and generally comprise dyed or colored thermoplastic powders, known in the art as toner particles, which are mixed with coarser carrier granules, such as ferromagnetic granules. The toner particles and carrier granules are selected such that the toner particles acquire the appropriate charge relative to the electrostatic latent image recorded on the photoconductive surface. When the developer mix is brought into contact with the charged photoconductive surface the greater attractive force of the electrostatic latent image recorded thereon causes the toner particles to transfer from the carrier granules and adhere to the electrostatic latent image.

Multi-color electrophotographic printing is substantially identical to the foregoing process of black and white printing. However, rather than forming a single latent image on the photoconductive surface, successive latent images corresponding to different colors are recorded thereon. Each single color electrostatic latent image is developed with toner particles of a color complimentary thereto. This process is repeated a plurality of cycles for differently colored images and their respective complimentarily colored toner particles. For example, a red filtered light image is developed with cyan toner particles, while a green filtered light image is developed with magenta toner particles and a blue filtered light image with yellow toner particles. Each single color toner powder image is transferred to the copy sheet in superimposed registration with the prior toner powder image. This creates a multi-layered toner powder image on the copy sheet. Thereafter, the multi-layered toner powder image is permanently affixed to the copy sheet creating a color copy. An illustrative electrophotographic printing machine for producing color copies is the Model No. 1005 made by the Xerox Corporation.

It is evident that in printing machines of this type, toner particles are depleted from the developer mixture. As the concentration of toner particles decreases, the density of the resultant copy degrades. In order to maintain the copies being reproduced at a specified minimum density, it is necessary to regulate the concentration of toner particles in the developer mixture. This is achieved by a closed loop servo system which regulates developability. Developability, as it pertains to an electrophotographic printing machine is the ability of the developer mixture to develop the latent image with at least a minimum specified density. It has long been recognized that a closed loop servo system, which regulates developability by measuring the density of the powder image developed on the photoconductive surface, optimizes cost and performance. This is due to the relative stability of the transfer and fusing processes. Also, by modulating one parameter, such as toner particle concentration, compensation for factors contributing to low copy quality, such as photoreceptor dark decay fluctuation and developer aging, can be partially accomplished. The use of densitometers for measuring the optical density of black toner particles is well known. However, densitometers used for black toner particles are generally unsuitable for use with colored toner particles. Densitometers of this type are generally sensitive to the large component of diffusely reflected flux in the infrared from colored toner particles which gives false density measurements. There do not appear to be any comparable densitometers for measuring the density of colored toner particles. Various approaches have been used to measure density. The following disclosures appear to be relevant.

U.S. Pat. No. 4,054,391
Patentee: Witte
Issued: October 18, 1977
U.S. Pat. No. 4,284,356
Patentee: Heilman
Issued: August 18, 1981
U.S. Pat. No. 4,553,033
Patentee: Hubble, III et al.
Issued: November 12, 1985

The relevant portions of the foregoing patents may be briefly summarized as follows:

US-A-4,054,391 discloses a specular reflectance micordensitometer wherein the amount of light specularly reflected by a test surface is correlated to the density of particle coverage on the surface. Light incident on the test surface from an illuminating microscope specularly reflects into a collecting microscope and is compared to the light reflected from a clean test surface. The reflectance of a clean photoreceptor surface and a toned photoreceptor surface is measured and the ratio determined.

US-A-4,284,356 describes light sources and light detectors for illuminating and comparing surface reflectivity. First and second reflects light beams are compared to determine the greater reflectivity of the first and second respective sheet surfaces. The light beams from the light source may be either collimated light beams or non-collimated (diffuse) light beams. The light detectors have an electrical output signal responsive to the intensity or density of the light beams incident thereon.

US-A-4,553,033 discloses an infrared reflectance densitometer including a light emitting diode, a collimating lens through which light is projected to a photosensitive surface, a collector lens and a field lens through which reflected light is focused onto a signal photodiode, and a control photodiode onto which a portion of reflected light is directed to control light output. The mount of light received on the signal photodiode is a measurement of the reflectance from the surface of the photoreceptor which, in turn, is proportional to the density of the toner particles thereon.

Pursuant to the features of the present invention, there is provided an apparatus for measuring the reduction in the specular reflectance of particles deposited on a surface. The apparatus includes means for projecting light rays onto the particles on the surface. Means are provided for detecting the total reflectivity of at least the particles and the diffuse component of the total reflectivity of at least the particles and generating a total signal indicative of the total reflectivity of at least the particles and a diffuse signal indicative of the diffuse component of the total reflectivity of at least the particles. Means, responsive to the difference between the total signal and the diffuse signal, generate a specular signal indicative of the specular component of the total reflectivity of at least the particles.

In accordance with another aspect of the present invention, there is provided an electrophotographic printing machine of the type in which the density of marking particles deposited on a moving photoconductive member is detected. The improvement includes means for projecting light rays onto the marking particles on the moving photoconductive member. Means are provided for detecting the total reflectivity of at least the marking particles and the diffuse component of the total reflectivity of at least the marking particles and generating a total signal indicative of the total reflectivity of at least the marking particles and a diffuse signal indicative of the diffuse component of the total reflectivity of at least the marking particles. Means, responsive to the difference between the total signal and the diffuse signal, generate a specular signal indicative of the specular component of the total reflectivity of at least the marking particles.

Another aspect of the present invention is an infrared densitometer for measuring the reduction in the specular component of the reflectivity of at least marking particles deposited on a moving photoconductive belt. The densitometer includes a collimating lens and a light source positioned to project light rays though the collimating lens onto the marking particles deposited on the moving photoconductive belt. A collector lens is positioned to receive the light rays reflected from at least the marking particles deposited on the moving photoconductive belt. A photosensor array is positioned to receive the light rays transmitted through the collector lens. The photosensor array generates a total signal proportional to the total reflectivity of at least the marking particles and a diffuse signal proportional to the diffuse component of the total reflectivity of at least the marking particles. Control circuitry, electrically connected to the photosensor array, compares the total signal and the diffuse signal to determine the difference therebetween for generating a specular signal proportional to the specular component of the total reflectivity of at least the marking particles.

Still another aspect of the present invention is a densitometer which includes a collimating lens. A light source is positioned to project light rays through the collimating lens. A collector lens is positioned to receive reflected light rays. A photosensor array is positioned to receive the reflected light rays transmitted through the collector lens. The photosensor array is adapted to generate a total signal proportional to the total flux of the light rays transmitted through the collector lens and a diffuse signal proportional to the diffuse component of the total flux of the light rays transmitted through the collector lens. Control circuitry, electrically connected to the photosensor array, compares the total signal and the diffuse signal to determine the difference therebetween for generating a specular signal proportional to the specular component of the total flux of the light rays transmitted through the collector lens.

Other aspects of the present invention will become apparent as the following description proceeds and upon reference to the drawings, in which:

While the present invention will hereinafter be described in connection with a preferred embodiment thereof, it will be understood that it is not intended to limit the invention to that embodiment. On the contrary, it is intended to cover all alternative, modifications and equivalents as may be included within the spirit and scope of the invention as defined by the appended claims.

Figure 1:
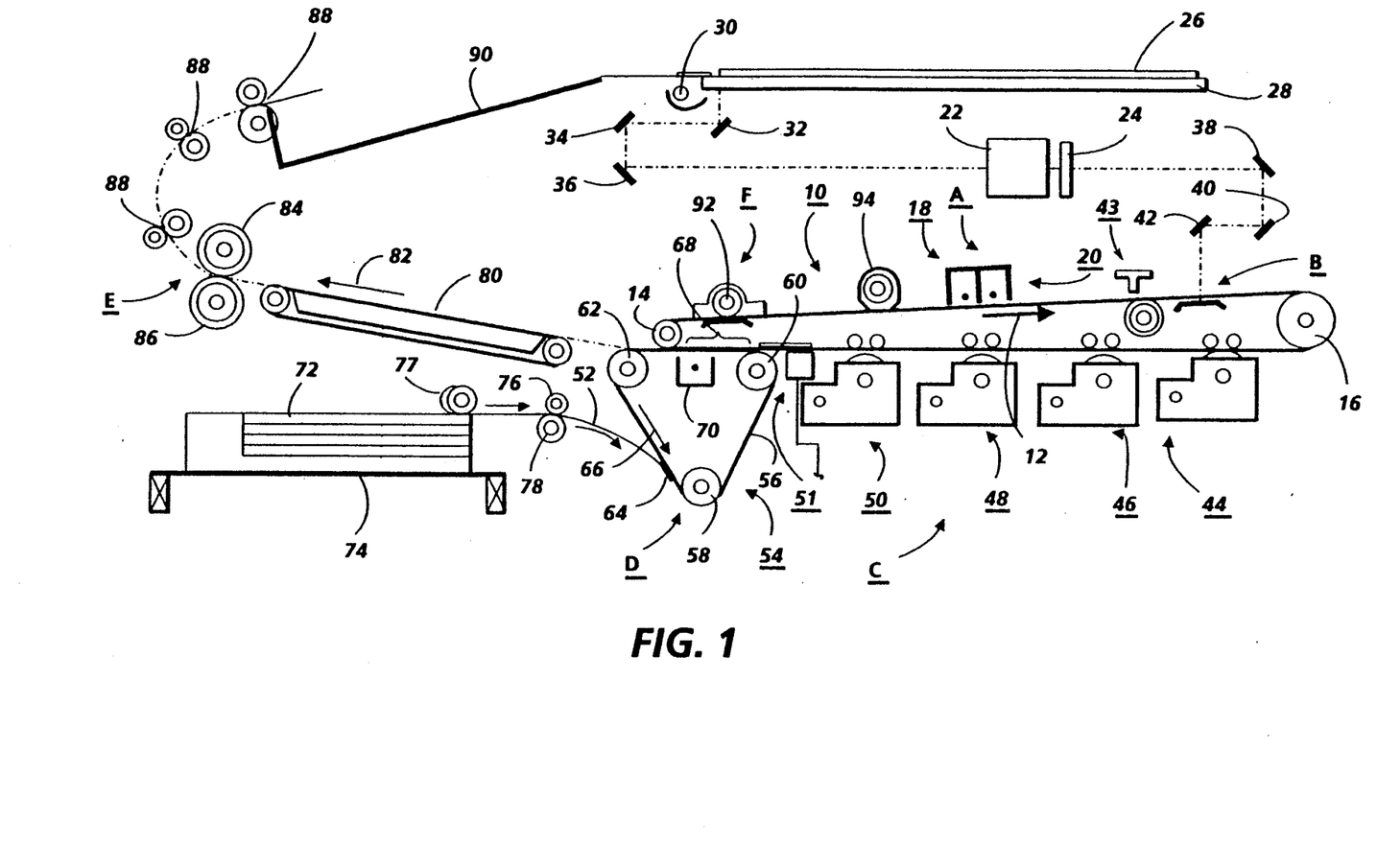
FIG. 1 is a schematic elevational view depicting an electrophotographic printing machine incorporating the infrared densitometer of the present invention therein.

For a general understanding of the features of the present invention, reference is made to the drawings. In the drawings, like reference numerals have been used throughout to designate identical elements. FIG. 1 schematically depicts the various components of an illustrative electrophotographic printing machine incorporating the infrared densitometer of the present invention therein. It will become evident from the following discussion that the densitometer of the present invention is equally well suited for use in a wide variety of electrostatographic printing machines, and is not necessarily limited in its application to the particular electrophotographic printing machine shown herein.

Inasmuch as the art of electrophotographic printing is well known, the various processing stations employed in the FIG. 1 printing machine will be shown hereinafter schematically and their operation described briefly with reference thereto.

As shown in FIG. 1, the electrophotographic printing machine employs a photoreceptor, i.e. a photoconductive belt 10. Preferably, the photoconductive belt 10 is made from a photoconductive material coated on a grounding layer, which, in turn, is coated on an anti-curl backing layer. The photoconductive material is made from a transport layer coated on a generator layer. The transport layer transports positive charges from the generator layer. The interface layer is coated on the grounding layer. The transport layer contains small molecules of di-m-tolydihenylbiphenyldiamine dispersed in a polycarbonate. The generation layer is made from trigonal selenium. The grounding layer is made form a titanium coated Mylar. The grounding layer is very thin and allows light to pass therethrough. Other suitable photoconductive materials, grounding layers, and anti-curl backing layers may also be employed. Belt 10 moves in the direction of arrow 12 to advance successive portions of the photoconductive surface sequentially through the various processing stations disposed about the path of movement thereof. Belt 10 is entrained about idler roller 14 and drive roller 16. Idler roller 14 is mounted rotatably so as to rotate with belt 10. Drive roller 16 is rotated by a motor coupled thereto by suitable means such as a belt drive. As roller 16 rotates, it advances belt 10 in the direction of arrow 12.

Initially, a portion of photoconductive belt 10 passes through charging station A. At charging station A, two corona generating devices, indicated generally by the reference numerals 18 and 20 charge photoconductive belt 10 to a relatively high, substantially uniform potential. Corona generating device 18 places all of the required charge on photoconductive belt 10. Corona generating device 20 acts as a leveling device, and fills in any areas missed by corona generating device 18.

Next, the charged photoconductive surface is rotated to exposure station B. Exposure station B includes a moving lens system, generally designated by the reference number 22, and a color filter mechanism, shown generally by the reference numeral 24. An original document 26 is supported stationarily upon a transparent viewing platen 28. Successive incremental areas of the original document are illuminated by means of a moving lamp assembly, shown generally by the reference numeral 30. Mirrors 32, 34 and 36 reflect the light rays through lens 22. Lens 22 is adapted to scan successive areas of illumination of platen 28. The light rays from lens 22 are reflected by mirrors 38, 40, and 42 to be focused on the charged portion of photoconductive belt 10. Lamp assembly 30, mirrors 32, 34 and 36, lens 22, and filter 24 are moved in a timed relationship with respect to the movement of photoconductive belt 10 to produce a flowing light image of the original document on photoconductive belt 10 in a non-distorted manner. During exposure, filter mechanism 24 interposes selected color filters into the optical light path of lens 22. The color filters operate on the light rays passing through the lens to record an electrostatic latent image, i.e. a latent electrostatic charge pattern, on the photoconductive belt corresponding to a specific color of the flowing light image of the original document. Exposure station B also includes a test area generator, indicated generally by the reference numeral 43, comprising a light source to project a test light image onto the charged portion of the photoconductive surface in the inter-image region, i.e. the region between successive electrostatic latent images recorded on photoconductive belt 10, to record a test area. The test area, as well as the electrostatic latent image recorded on the photoconductive surface of belt 10 are developed with toner particles at the development stations.

After the electrostatic latent image and test area have been recorded on photoconductive belt 10, belt 10 advances them to development station C. Development station C includes four individual developer units generally indicated by the reference numerals 44, 46, 48 and 50. The developer units are of a type generally referred to in the art as "magnetic brush development units." Typically, a magnetic brush development system employs a magnetizable developer material including magnetic carrier granules having toner particles adhering triboelectrically thereto. The developer material is continually brought through a directional flux field to form a brush of developer material. The developer particles are continually moving so as to provide the brush consistently with fresh developer material. Development is achieved by bringing the brush of developer material into contact with the photoconductive surface. Developer units 44, 46 and 48, respectively, apply toner particles of a specific color which corresponds to the compliment of the specific color separated electrostatic latent image recorded on the photoconductive surface. The color of each of the toner particles is adapted to absorb light within a preselected spectral region of the electromagnetic wave spectrum corresponding to the wave length of light transmitted through the filter. For example, an electrostatic latent image formed by passing the light image through a green filter will record the red and blue portions of the spectrums as areas of relatively high charge density on photoconductive belt 10, while the green light rays will pass through the filter and cause the charge density on the photoconductive belt 10 to be reduced to a voltage level ineffective for development. The charged areas are then made visible by having developer unit 44 apply green absorbing (magenta) toner particles onto the electrostatic latent image recorded on photoconductive belt 10. Similarly, a blue separation is developed by developer unit 46 with blue absorbing (yellow) toner particles, while the red separation is developed by developer unit 48 with red absorbing (cyan) toner particles. Developer unit 50 contains black toner particles and may be used to develop the electrostatic latent image formed from a black and white original document. Each of the developer units is moved into and out of the operative position. In the operative position, the magnetic brush is closely adjacent the photoconductive belt, while, in the non-operative position, the magnetic brush is spaced therefrom. During development of each electrostatic latent image only one developer unit is in the operative position, the remaining developer units are in the non-operative position. This insures that each electrostatic latent image and successive test areas are developed with toner particles of the appropriate color without co-mingling. In FIG. 1, developer unit 44 is shown in the operative position with developer units 46, 48 and 50 being in the non-operative position. The developed test area passes beneath an infrared densitometer, indicated generally by the reference number 51. Infrared densitometer 51 is positioned adjacent the photoconductive surface of belt 10 to generate electrical signals proportional to the developed toner mass of the test area. The detailed structure of densitometer 51 will be described hereinafter with reference to FIGS. 2 through 5, inclusive.

After development, the toner image is moved to transfer station D where the toner image is transferred to a sheet of support material 52, such as plain paper amongst others. At transfer station D, the sheet transport apparatus, indicated generally by the reference numeral 54, moves sheet 52 into contact with photoconductive belt 10. Sheet transport 54 has a pair of spaced belts 56 entrained about three rolls 58, 60 and 62. A gripper 64 extends between belts 56 and moves in unison therewith. Sheet 52 is advanced from a stack of sheets 72 disposed on ray 74. Feed roll 77 advances the uppermost sheet from stack 72 into the nip defined by forwarding rollers 76 and 78. Forwarding rollers 76 and 78 advance sheet 52 to sheet transport 54. Sheet 52 is advanced by forwarding rollers 76 and 78 in synchronism with the movement of gripper 64. In this way, the leading edge of sheet 52 arrives at a preselected position to be received by the open gripper 64. The gripper then closes securing the sheet thereto for movement therewith in a recirculating path. The leading edge of the sheet is secured releasably by gripper 64. As the belts move in the direction of arrow 66, the sheet 52 moves into contact with the photoconductive belt, in synchronism with the toner image developed thereon, at the transfer zone 68. A corona generating device 70 sprays ions onto the backside of the sheet so as to charge the sheet to the proper magnitude and polarity for attracting the toner image from photoconductive belt 10 thereto. Sheet 52 remains secured to gripper 64 so as to move in a recirculating path for three cycles. In this way, three different color toner images are transferred to sheet 52 in superimposed registration with one another. Thus, the aforementioned steps of charging, exposing, developing, and transferring are repeated a plurality of cycles to form a multi-color copy of a colored original document.

After the last transfer operation, grippers 64 open and release sheet 52. Conveyor 80 transports sheet 52, in the direction of arrow 82, to fusing station E where the transferred image is permanently fused to sheet 52. Fusing station E includes a heated fuser roll 84 and a pressure roll 86. Sheet 52 passes through the nip defined by fuser roll 84 and pressure roll 86. The toner image contacts fuser roll 84 so as to be affixed to sheet 52. Thereafter, sheet 52 is advanced by forwarding roll pairs 88 to catch tray 90 for subsequent removal therefrom by the machine operator.

The last processing station in the direction of movement of belt 10, as indicated by arrow 12 is cleaning station F. A rotatably mounted fibrous brush 92 is positioned in cleaning station F and maintained in contact with photoconductive belt 10 to remove residual toner particles remaining after the transfer operation. Thereafter, lamp 94 illuminates photoconductive belt 10 to remove any residual charge remaining thereon prior to the start of the next successive cycle.

Figure 2:
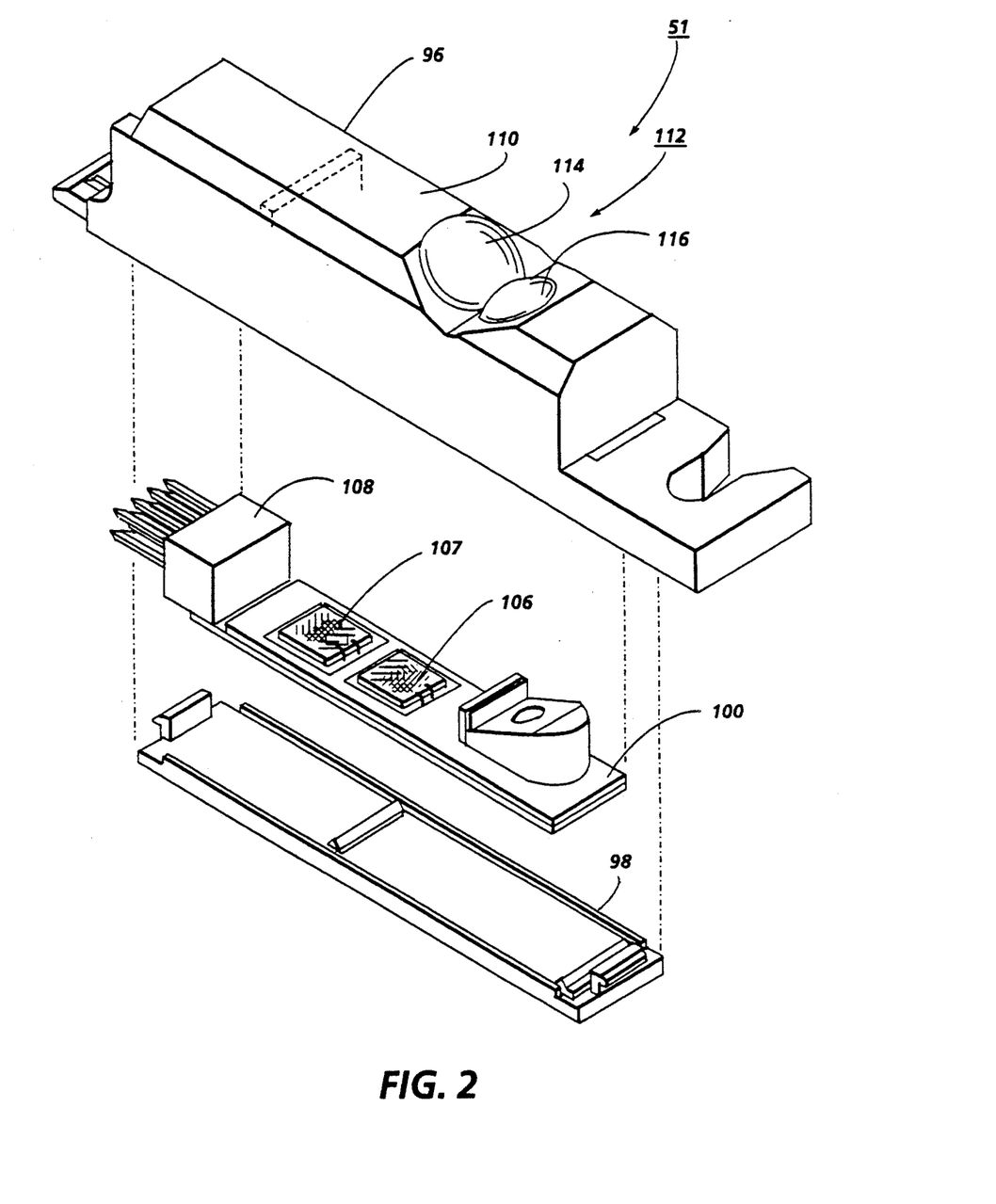
FIG. 2 is a schematic perspective view showing the densitometer used in the FIG. 1 printing machine.
Figure 3:
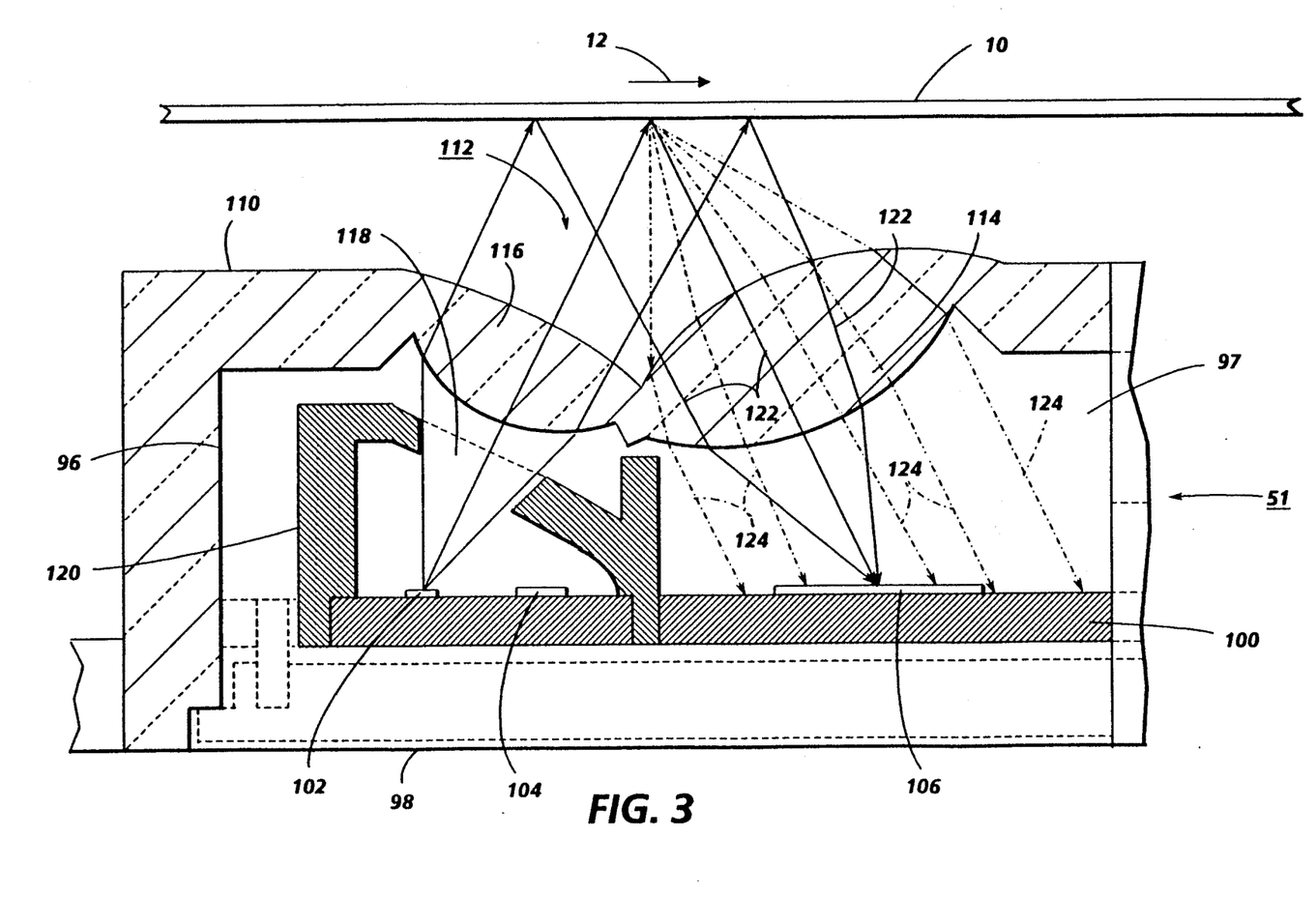
FIG. 3 is a fragmentary, sectional elevational view of the FIG. 2 densitometer.

Referring now to FIGS. 2 and 3, there is shown infrared densitometer 51 in greater detail. Densitometer 51 includes a generally rectangularly shaped molded housing 96 made preferably from an acrylic material or any other suitable optically transparent material. Housing 96 defines a chamber 97. A cover 98 encloses the bottom of housing 96. A printed circuit writing board 100 is mounted between cover 98 and housing 96 in chamber 97. Printed circuit board 100 supports a suitable light emitting diode (LED) 102 for providing light rays to illuminate the marking particles adhering to the photoconductive surface of belt 10. A control photodiode 104 and a photodiode array 106 are also mounted on printed circuit board 100. The details of photodiode array 106 will be described hereinafter with reference to FIG. 4. Connector 108 is also mounted on printed circuit board 100. An integrated circuit chip, indicated generally by the reference numeral 107, is electrically connected to LED 102, photodiode 104 and photodiode array 106 to provide drive current to LED 102 and to process the signals from photodiode 104 and photodiode array 106. The top surface 110 of housing 96 defines a V-shaped recess, generally indicated by the reference numeral 112. One surface of the V-shaped recess 112 supports a condenser lens 116 which is an integral collimating lens. The other surface of the V-shaped recess 112 supports another condenser lens 114 which is an integral collector lens. LED 102 generates near infrared light rays which are transmitted through an aperture 118 in cavity 120 onto condenser lens 116. Condenser lens 116 collimates the light rays and focuses the light rays onto the marking or toner particles deposited on the test area recorded on the photoconductive surface of belt 10. Photodiode 104 is positioned to receive a portion of the LED radiant flux reflected from the walls of cavity 120. The output signal from photodiode 104 is compared with a reference signal and the resultant error signal used to regulate the input current to LED 102 to compensate for LED aging and thermal effects. The light rays reflected from the toner particles are collected by condenser lens 114 and directed onto the surface of photodiode array 106. The specular component of the reflected light rays or flux, as shown by arrows 122, is focused on a small spot on surface of the central segment of photodiode array 106. The diffuse components of the reflected light rays or flux, as shown by arrows 124, flood the entire surface of photodiode array 106. Further details of the structure of the densitometer, exclusive of photodiode array 106, may be found in U.S. Pat. No. 4,553,033 issued to Hubble, III et al. on Nov. 12, 1985, the relevant portions thereof being hereby incorporated into the present application.

Figure 4:
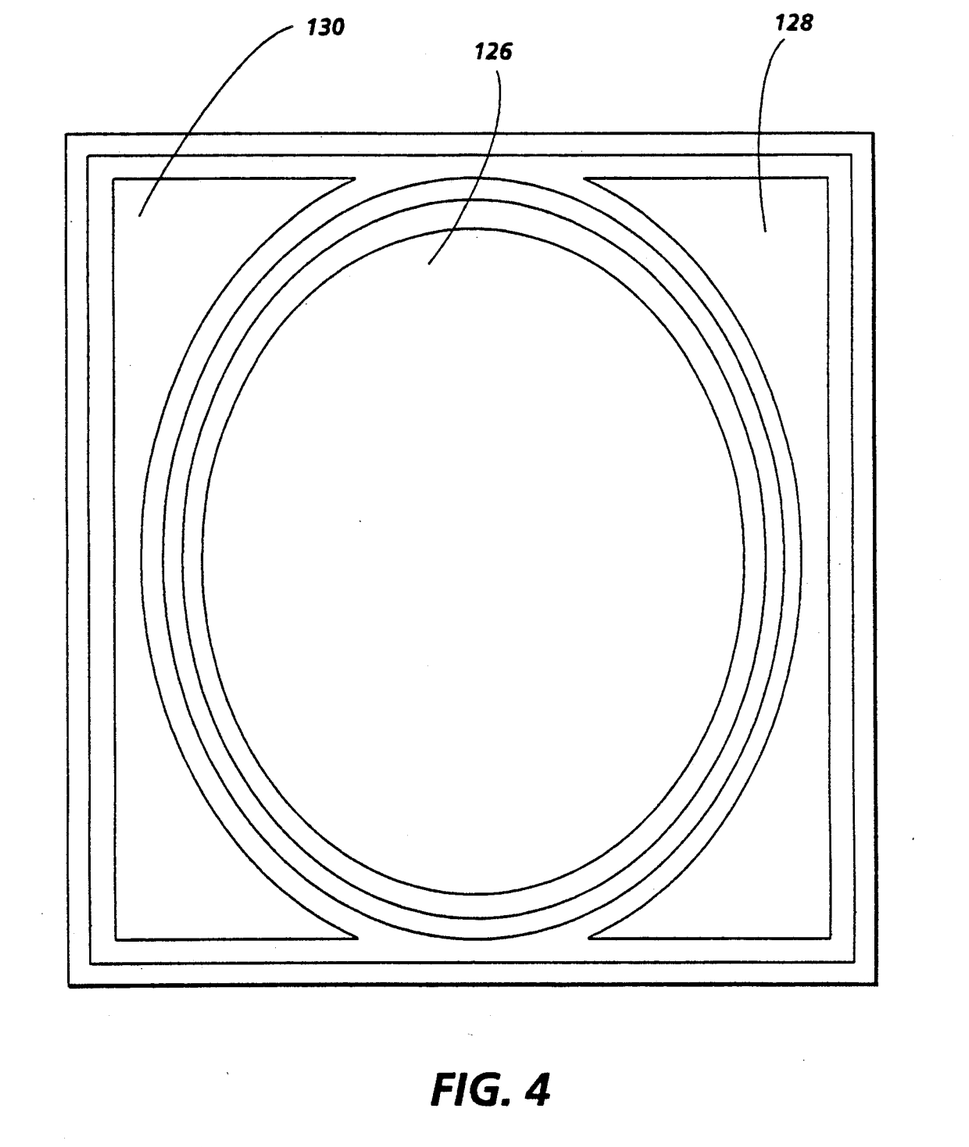
FIG. 4 is an enlarged plan view of the photodiode array used in the FIG. 3 densitometer.

Turning now to FIG. 4, there is shown photodiode array 106 in greater detail. Preferably, photodiode 106 is about 5 millimeter square. Photodiode array 106 receives the light rays transmitted through condenser lens 116. These light rays are reflected from the toner particles adhering to the photoconductive surface of belt 10 and the exposed portion of the photoconductive surface of belt 10. A central photodiode 126 receives the total reflected light rays or flux. The total reflected light rays or flux includes the specular component and the diffuse component of the reflected light rays or flux. Thus, central photodiode 126 generates an electrical signal proportional to the total reflected flux including the diffuse component and the specular component thereof. As shown, central photodiode 126 is preferably substantially elliptical. Edge photodiodes 128 and 130 are configured to compliment central photodiode 126 to complete photodiode array 106 which is substantially square in shape. Edge photodiodes 128 and 130 are substantially identical to one another, being shaped as mirror images of one another. Edge photodiodes 128 and 130 are positioned to receive only the diffuse component of the reflected light rays or flux transmitted through condenser lens 116. Hence, the electrical signal generated by edge photodiodes 128 and 130 is proportional to only the diffuse component of the reflected light rays or flux. Subtraction of the combined electrical signals of the edge photodiodes from the electrical signal from the central photodiode yields a resultant electrical signal proportional to the specular component of the light rays or flux reflected from the toner particles and the exposed portion of the photoconductive surface of belt 10. A block diagram reflecting the integrated circuit 107 used to measure the specular component of the light rays is shown in FIG. 5.

Figure 5:
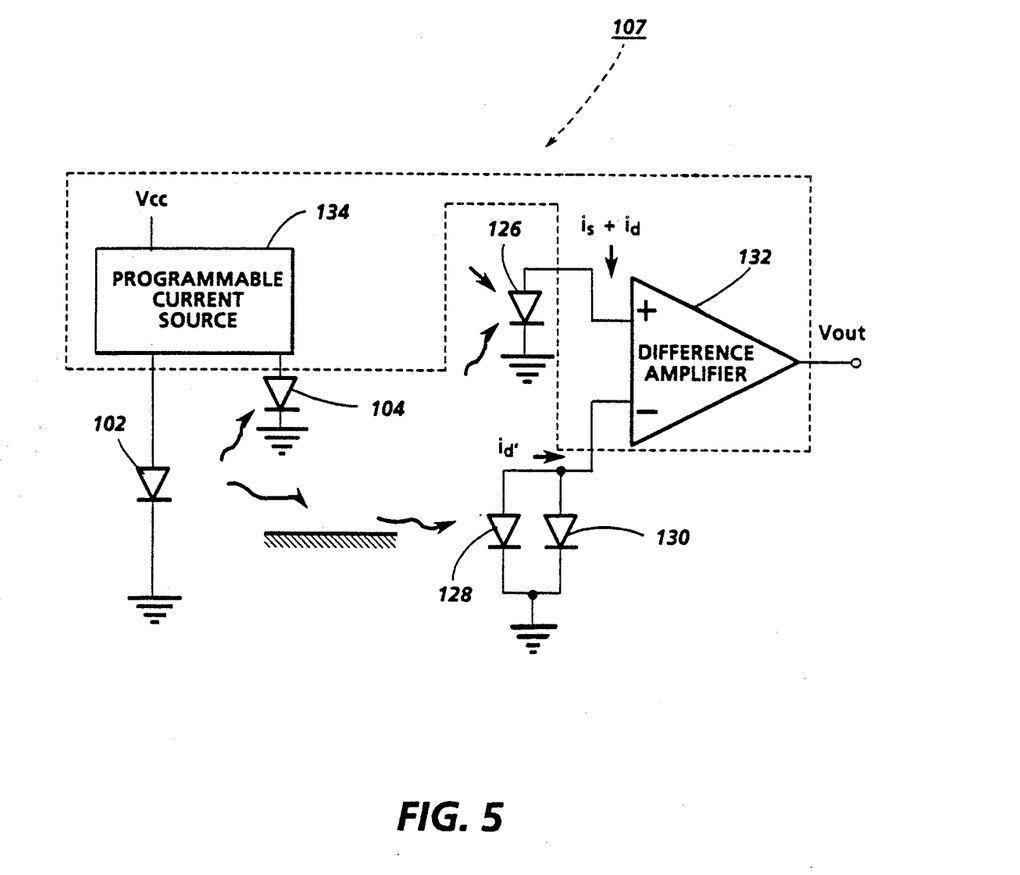
FIG. 5 is a block diagram of the control logic associated with the FIG. 3 densitometer.

As shown in FIG. 5, central photodiode 126 generates an electrical signal proportional to the the sum of the specular and diffuse components of the light rays. Central photodiode 126 is electrically connected to difference amplifier 132. The electrical output signals from photodiodes 128 and 130 are proportional to the diffuse component of the light rays. Photodiodes 128 and 130 are electrically connected to difference amplifier 132. The electrical signals from photodiodes 128 and 130 are combined and transmitted to difference amplifier 132. The voltage output, $V_{out}$, from difference amplifier 132 may be expressed as:

$$V_{out} = G_1(i_s + i_d) - G_2(i_{d'})$$

where

G$_1$ and G$_2$ are gains of difference amplifier 132;

$i_s$ is the specular component of the current output from central photodiode 126;

$i_d$ is the diffuse component of the current output from central photodiode 126; and $i_{d'}$ is the diffuse components of the combined current output from edge photodiodes 128 and 130.

G$_1$ and G$_2$ are set such that $$G_1(i_d) = G_2(i_{d'}).$$

This yields $$V_{out} = G_1(i_s).$$

Thus, the voltage output from difference amplifier 132 is proportional only to the specular component of the current output. This voltage output provides a measure of the area coverage of colored toner particles deposited on the photoconductive surface. This may be seen more clearly from the following Table which provides the approximate reflective properties of selected photoreceptor and toner materials at 880 nanometers incident wavelength.

| SURFACE | SPECULAR REFLECTIVITY | DIFFUSE REFLECTIVITY |
| --- | --- | --- |
| Photoreceptor | 5-16% | 12-26% |
| Yellow Toner | 0% | 60% |
| Magenta Toner | 0% | 64% |
| Cyan Toner | 0% | 44% |
| Black Toner | 0% | 1% |

Thus, when 100% of the test area is developed with toner particles, the specular reflectivity is zero and the output from difference amplifier 132 will be zero. When the test area is undeveloped, i.e. 0% of the test area is developed with toner particles, the output will correspond to the specular reflectivity of the photoreceptor whose specular reflectivity is non-zero.

With continued reference to FIG. 5, the electrical signal from control photodiode 104 is transmitted through suitable circuitry to generate a voltage output which regulates a current source 134. The current source energizes LED 102. In this way, a feedback loop is formed for driving LED 102 to provide a relatively constant output. Thus, if the signal from photodiode changes, the output from current source 134 is suitably adjusted to maintain a relatively constant light output from the LED 102.

In recapitulation, the densitometer of the present invention detects the total and diffuse components of the reflectivity of the light rays. The difference is obtained and a signal generated proportional to the specular component of the reflectivity of the light rays generated. In this way, the densitometer is capable of sensing the presence or absence of both colored or black toner particles on a photoreceptor surface.

It is, therefore, evident that there has been provided in accordance with the present invention, a densitometer that fully satisfies the aims and advantages hereinbefore set forth. While this invention has been described in conjunction with a specific embodiment thereof, it is evident that many alternative, modifications and variations will be apparent to those skilled in the art. Accordingly, it is intended to embrace all such alternatives, modifications and variations as fall within the spirit and broad scope of the appended claims.

What is claimed is:

1. A densitometer used in an electrophotographic printing machine to measure the reduction in the specular component of the reflectivity of marking particles deposited on a moving photoconductive belt wherein said densitometer, including:

a collimating lens;

a light source positioned to project light rays through said collimating lens;

a collector lens positioned to receive reflected light rays;

a photosensor array positioned to receive the reflected light rays transmitted through said collector lens and being adapted to generate a total signal proportional to the total flux of the light rays transmitted through said collector lens and a diffuse signal proportional to the diffuse component of the total flux of the light rays transmitted through said collector lens; and control circuitry, electrically connected to said photosensor array, for comparing the total signal and the diffuse signal to determine the difference therebetween for generating a specular signal proportional to the specular component of the total flux of the light rays transmitted through said collector lens.

2. A densitometer according to claim 1, wherein said photosensor array includes:

a central photosensor positioned to receive the total flux of the light rays transmitted through said collector lens; and at least one edge photosensor positioned about the periphery of said central photosensor to receive the diffuse component of the total flux of the light rays transmitted through said collector lens.

3. A densitometer according to claim 2, wherein said light source includes a light emitting diode.

4. A densitometer according to claim 3, wherein:

said central photosensor includes a central photodiode; and said edge photosensor includes an edge photodiode.

5. A densitometer according to claim 4, further including means for measuring and controlling the intensity of the light rays being emitted from said light source.

6. A densitometer according to claim 5, wherein said measuring and controlling means includes a control photosensor positioned adjacent said light source to detect the variation in intensity of the light rays being emitted from said light source.

* * * * *